United States Patent
Feral et al.

(10) Patent No.: US 11,311,484 B2
(45) Date of Patent: Apr. 26, 2022

(54) METHODS AND COMPOSITIONS FOR TREATING SKIN AFFLICTIONS

(71) Applicants: INSERM (INSTITUT NATIONAL DE LA SANTÉ ET DE LA RECHERCHE MÉDICALE), Paris (FR); UNIVERSITÉ COTE D'AZUR, Nice (FR); CENTRE NATIONAL DE LA RECHERCHE SCIENTIFIQUE (CNRS), Paris (FR)

(72) Inventors: Chloé Feral, Nice (FR); Floriane Tissot, Mauleon (FR); Laurence Cailleteau, Nice (FR); Soline Estrach, Nice (FR)

(73) Assignees: INSERM (Institut National de la Santé et de la Recherche Médicale), Paris (FR); Université Nice Sophia Antipolis, Nice (FR); Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 17/052,327

(22) PCT Filed: Apr. 30, 2019

(86) PCT No.: PCT/EP2019/061074
§ 371 (c)(1),
(2) Date: Nov. 2, 2020

(87) PCT Pub. No.: WO2019/211285
PCT Pub. Date: Nov. 7, 2019

(65) Prior Publication Data
US 2021/0161816 A1    Jun. 3, 2021

(30) Foreign Application Priority Data

May 2, 2018  (EP) .................................. 18170458

(51) Int. Cl.
*A61K 9/127* (2006.01)
*A61P 17/02* (2006.01)
*A61K 9/00* (2006.01)
*A61K 35/12* (2015.01)

(52) U.S. Cl.
CPC ............ *A61K 9/127* (2013.01); *A61K 9/0014* (2013.01); *A61K 35/12* (2013.01); *A61P 17/02* (2018.01)

(58) Field of Classification Search
None
See application file for complete search history.

(56) References Cited

PUBLICATIONS

Feral et al: "CD98hc (SLC3A2) participates in fibronectin matrix assembly by mediating integrin signaling,I", The Journal of Cell Biology, vol. 178, No. 4, pp. 701-711, Aug. 13, 2007.
Lematre et al: "CD98hc (SLC3A2) is a key regulator of keratinocyte adhesion", Journal of Dermatological Science, vol. 61, No. 3, pp. 169-179, Dec. 24, 2010.
Lin'kova et al: "Peptide Regulation of Skin Fibroblast Functions during Their Aging In Vitro", Bulletin of Experimental Biology and Medicine, vol. 161, No. 1 pp. 175-178, Jun. 4, 2016.

*Primary Examiner* — Nannette Holloman
(74) *Attorney, Agent, or Firm* — WCF IP

(57) ABSTRACT

The present invention relates to a method for treating skin afflictions in a subject comprising a step of administering said subject with a therapeutically effective amount of small extracellular vesicles (sEV) comprising CD98hc. Inventors have demonstrated that healthy dermal fibroblasts produced and secreted EVs bearing characteristic of exosome-like small EVs (sEVs). They have shown that CD98hc was present at the surface of sEVs, transferred and stabilized at the plasma membrane of recipient cells. They observed that the transferred protein was functional both in vitro and in vivo. Furthermore, injection of sEVs in epidermal CD98hc KO mice exhibiting wound healing defect rescued wound closure in vivo. Thus, their findings reveal that CD98hc contained in EVs could potentially be used in vivo to treat and improve multiple skin afflictions by allowing protein rescue.

9 Claims, 2 Drawing Sheets

METHODS AND COMPOSITIONS FOR TREATING SKIN AFFLICTIONS

FIELD OF THE INVENTION

Figure 1A:
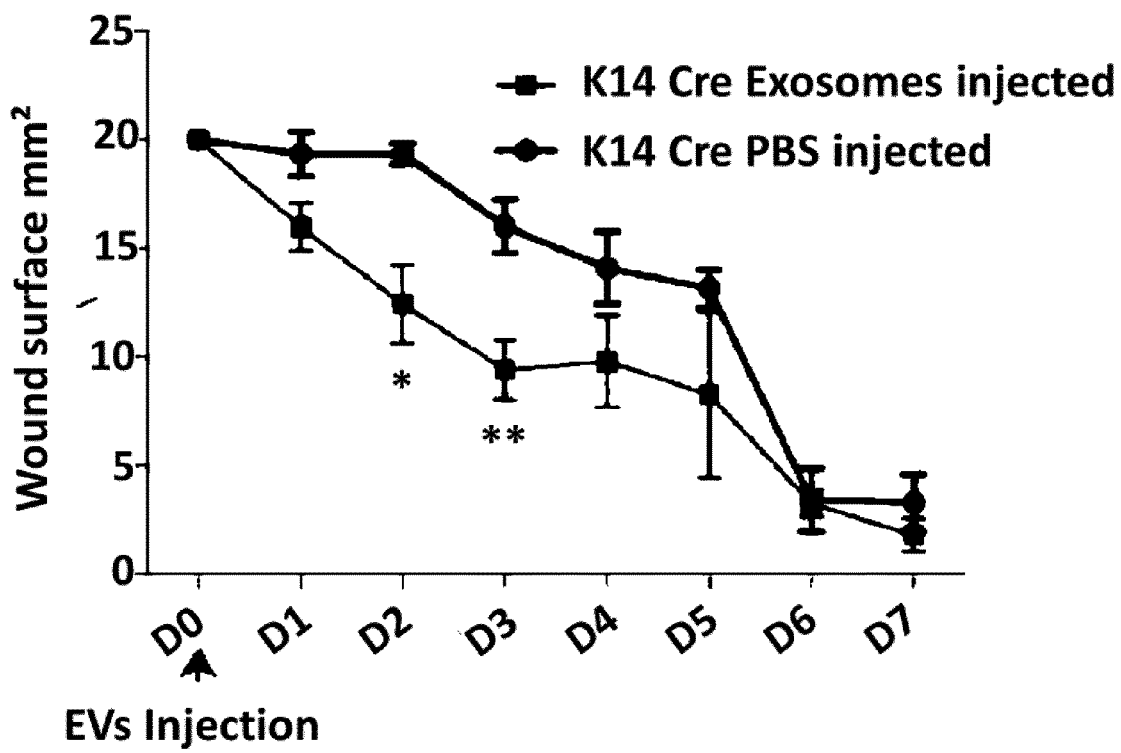

The present invention is in the field of dermatology. More particularly, the invention relates to methods and composition for treating skin afflictions and improving wound healing.

BACKGROUND OF THE INVENTION

Wound healing is a process which starts immediately after an injury and may continue for months or years, and is essentially the same for all types of wounds. Variations in wound healing are the result of differences in location, severity of the wound, and the extent of injury to the tissues. Other factors affecting wound healing are the age, nutritional status and general state of health of a subject and its body reserves and resources for the regeneration of tissue. The human adult wound healing process can be divided into 3 or 4 distinct phases: (i) coagulation and haemostasis; (ii) inflammation; (iii) proliferation; and (iv) wound remodelling with scar tissue formation. Wound healing involves multiple cell populations, the extracellular matrix and the action of soluble mediators such as growth factors and cytokines. Extracellular vesicles (EV) mediate intercellular communication, and as such play an important role both in health and disease (Colombo et al., 2014). They are composed of a lipid bilayer and contain cytosolic protein and RNA. Inventors previously showed that CD98hc, a dual function transmembrane protein interacting with both amino acid transporters of the HAT family and integrins, is implicated in the maintenance of epidermis homeostasis during aging as well as in keratinocyte tumorigenesis (Boulter et al., 2013; Estrach et al., 2014). However, whether EVs could participate to an early cellular response by efficiently transferring functional proteins is still unknown.

SUMMARY OF THE INVENTION

The invention relates to a method for treating skin afflictions in a subject comprising a step of administering to said subject a therapeutically effective amount of small extracellular vesicles (sEV) comprising CD98hc. In particular, the invention is defined by the claims.

DETAILED DESCRIPTION OF THE INVENTION

Inventors have found that small Extracellular vesicles (EVs) can transfer functional signaling hub through their lipid bilayer and participate to skin homeostasis. They have identified CD98hc, a dual function transmembrane protein, implicated in epidermis homeostasis, as an important mediator of EV-based intercellular communication in vivo. They first demonstrated that healthy dermal fibroblasts produced and secreted EVs bearing characteristic of exosome-like small EVs (sEVs). They have shown that CD98hc was present at the surface of sEVs, transferred and stabilized at the plasma membrane of recipient cells. They observed that the transferred protein was functional both in vitro and in vivo. Furthermore, injection of sEVs in epidermal CD98hc KO mice exhibiting wound healing defect rescued wound closure in vivo. Thus, their findings reveal that CD98hc contained in EVs could potentially be used in vivo to treat and improve multiple skin afflictions by allowing protein rescue.

Accordingly, the invention relates to a method for treating skin afflictions in a subject comprising a step of administering to said subject a therapeutically effective amount of small extracellular vesicles (sEV) comprising CD98hc.

As used herein, the terms "treating" or "treatment" refer to both prophylactic or preventive treatment as well as curative or disease modifying treatment, including treatment of subject at risk of contracting the disease or suspected to have contracted the disease as well as subject who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at regular intervals, e.g., weekly, monthly, yearly, etc.) or intermittent therapy (e.g., interrupted treatment, intermittent treatment, treatment at relapse, or treatment upon achievement of a particular predetermined criteria [e.g., pain, disease manifestation, etc.]).

As used herein, the term "skin" refers to any mammal skin, nail, and mucosal surfaces that can suffer from various forms of disease and infection and are usually at least partially exposed to the environment, such as skin, nails, lips, and mucosa. As used herein, the term "skin afflictions" also known as skin disorders, refers to any of a number of skin ailments and infections that afflict the skin surface or deeper skin tissue, including inflammatory skin disease (e.g., acne, eczema, dermatitis, poison ivy, psoriasis, pyoderma gangrenosum, rosacea, hives, inflamed burns, etc.); bacterial skin infection (e.g., impetigo, folliculitis, furunculosis, carbunculosis, ecthyma, erysipelas, cellulitis, necrotizing fasciitis, etc.); fungal and yeast infection (e.g., dermatophytosis, candidiasis, tinea, athlete's foot, nail fungal infection, diaper rash, etc.); viral infection (e.g., herpes simplex, herpes zoster, cold sores, warts, molluscum contagiosum, etc.); and infection caused by small macro organisms such as mites (e.g,. face mites such as demodex folliculorum, Demodex brevis, Demodex canis, etc.), insects, animals (bites), etc. In another embodiment, the skin disorder is related to diabetes. Example of diabetes related skin disorders are:

acanthosis nigricans; diabetic dermopathy; necrobiosis lipoidica diabeticorum; allergic reactions; diabetic blisters; eruptive xanthomatosis; digital sclerosis; or disseminated granuloma annulare. In a particular embodiment, the skin disorder is an ulcer which is characterized by a sore on the skin or a mucous membrane. The term "ulcer" refers to a break in skin or mucous membrane with loss of surface tissue, disintegration and necrosis of epithelial tissue, and often pus. Typically, the ulcer is selected from the group consisting of: pressures ulcers (bedsores), genital ulcer, ulcerative dermatitis, ana fissure, diabetic foot ulcer, corneal ulcer, mouth ulcer (e.g. aphtous ulcer), peptic ulcer, venous ulcer, stress ulcer, ulcerative sarcoidosis, ulcerative lichen planus or ulcerative colitis. In another embodiment, the skin affliction refers to injury in aged skin.

In a particular embodiment, the skin afflictions as described above cause wound healing. The method according to the invention is suitable to improve wound healing.

As used, herein, the term "wound" refers to a break or discontinuity in the structure of an organ or tissue, including epithelium, connective tissue, and muscle tissue, caused by an external agent. Examples of wounds include, but are not limited to, skin wounds, bruises, ulcerations, bedsores, grazes, tears, cuts, punctures, psoriasis wounds, tympanic membrane perforations, and burns. Wound healing is a dynamic, interactive process involving soluble mediators, blood cells, extracellular matrix, and parenchymal cells. Wound healing has 3 phases that overlap in time: vascular phase and inflammation, new tissue formation including reepithelialization, and tissue remodelling. Wounds are currently treated by applying an emergency treatment to a wounded site and waiting for the wounds to spontaneously heal via the biological recovering power of their own. In elderly persons, the process of wound healing is slowed and all phases of wound healing are affected. Accordingly, in a further embodiment, the method of the invention is suitable to use and to accelerate the wound healing process in an elderly person.

As used herein, the term "improve" refers to "promote" or "enhance" the wound healing generally means increasing the speed by which the wound or perforation heals or reducing the extent of residual scar or necrotic tissue during or after healing of the wound or perforation.

As used herein, the term "subject" refers to any mammals, such as a rodent, a feline, a canine, and a primate. Particularly, in the present invention, the subject is a human afflicted with or susceptible to be afflicted with at least one of skin afflictions as described above. More particularly, the subject is afflicted with or susceptible to be afflicted with at least one skin affliction as described above. More particularly, the subject has the difficulties to heal a wound generated by one of the skin afflictions as described above.

As used herein, the term "CD98" is a heterodimer, in which a unique common heavy chain (4F2hc, CD98hc, SLC3A2) associates with one of several light chains composed of multiple membrane-spanning domains (Devés and Boyd, 2000). This glycoprotein is considered as an amino acid (AA) transporter (together with another subunit) and integrin signaling enhancer. The term "CD98hc" also known as SLC3A2, refers to CD98 heavy chain.

As used herein, the term "small extracellular vesicles" (sEV) refers to membrane-enveloped vesicles produced in an evolutionally conserved fashion by a variety of cells found in different organisms and species. Extracellular vesicles can be broadly classified into 3 main classes: (a) microvesicles/microparticles/ectosomes that are produced by outward budding and fission of the plasma membrane; (b) exosomes that are formed within the endosomal network and released upon fusion of multi-vesicular bodies with the plasma membrane; and (c) apoptotic bodies are released as blebs of cells undergoing apoptosis. Lower organisms, such as bacteria and parasites, are also able to secrete EVs. The major role of small extracellular vesicles is their ability to transfer information from the original cell to other cells using different classes of molecules. In humans, EVs can be found in all bodily fluids (e.g. cerebrospinal fluid, nasal secretion, saliva, balf, breast milk, synovial fluid, bile, blood, amniotic fluid, seminal fluid, uterine fluid, urine, faeces) and sometimes in intercellular regions. In a particular embodiment, the sEVs can be found in dermal fibroblast (Thery et al. 2006), induced pluripotent stem cell-derived mesenchymal stem cells (Zhang et al., 2015) or from adipose mesenchymal stem cells (Hu et al., 2016). Their size ranges between 20 nm and 1000 nm. In a particular embodiment, the size ranges between 30 nm and 150 nm. They are composed of a lipid bilayer and contain cytosolic protein and RNA. In a particular embodiment, the sEV are selected from the group consisting of but not limited to natural vesicles such as exosomes, liposomes or synthetic vesicles such as nanoparticles.

Example of Method to Obtain Natural Vesicles such as Exosomes

The small EVs (sEVs) can be obtained from dermal fibroblast (DF) as described in Thery et al. 2006 2015 and Keriel et al., 2015. Such sEVs can be obtained from a healthy subject. Then, they are analyzed: to do so, conditioned media are collected from DF after 24 hours of incubation in medium without serum. sEVs were isolated by differential ultracentrifugation, as described in Théry et al., 2001. The sEVs correspond to the pellet obtained after 100,000×g ultracentrifugation, as defined by Kowal et al., 2016 who performed proteomic comparisons of EVs population. Exosomes are part of this population of sEVs (Kowal et al., 2016). The particle size distribution and concentration are measured by NanoSight analysis. The sEVs as obtained are purified by ExoPen construct as described in WO2017083286. The sEVs can then be transferred in a subject suffering from one of the skin afflictions as described above.

In a particular embodiment, the sEVs are obtained from a subject suffering from one of the skin afflictions as described above. Then, they are modified to express the functional protein CD98hc and re-injected in the said subject. Typically, a vector can be used to express the CD98hc in the isolated vesicles. This type of vector contains any self-replicating polynucleotide sequence encoding for a biologically active molecule, e.g., RNA, DNA, protein, or peptide. In general, the vectors useful in the invention include, but are not limited to, plasmids, phagemids, viruses, other vehicles derived from viral or bacterial sources that have been manipulated by the insertion or incorporation of the sequence encoding CD98hc. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Example of Method to Obtain Synthetic Vesicles such as Polymeric Micro/Nanoparticles or Liposomes Polymeric micro/nanoparticles refer to micron to nano sized drug particles coated with layer(s) of polymer(s) and/or other materials. A polymer is a large molecule, or macromolecule, composed of many repeated subunits. The molecular weight can range from 500 to >100,000 Daltons. A biodegradable polymer defined in the biodegradable micro/nanoparticles section is preferred for use in this invention. The Z-average mean diameter of the polymeric particles of this invention range from 100 micron to below 100 nm, preferably from 50 micron to 10 micron, more preferably from 10 micron to 2 micron, still more preferably from 2 micron to 500 nm, even more preferably from 500 nm to 100 nm, and most preferably below 100 nm. Biodegradable polymeric nanoparticles where the drug is coated by polymeric materials are deemed to be very efficient drug delivery systems. It should be highlighted that the liberation of the polymer encapsulated drug can be carefully controlled by total surface area or the particle size, or the coating materials; and the drug concentration in the target site is maintained within the therapeutic window. Biodegradable polymers are considered as ideal biomaterials for the development of controlled- and sustained-release drug delivery systems as well as therapeutic devices.

A liposome is a spherical vesicle having at least one lipid bilayer, which fall in the category of microparticles or nanoparticles. Liposomes can be prepared by disrupting biological membranes (such as by sonication). Liposomes are most often composed of phospholipids, especially phosphatidylcholine, but may also include other lipids, such as egg phosphatidylethanolamine, so long as they are compatible with lipid bilayer structure. Lipid complexation with drug and other materials is also regarded as liposome in this invention. A liposome design may employ surface ligands for attaching to unhealthy tissue. The CD98hc could be incorporated into the liposome in either hydrophilic or hydrophobic region or both. The major types of liposomes are the multilamellar vesicles (MLV, with several lamellar phase lipid bilayers), the small unilamellar liposome vesicles (SUV, with one lipid bilayer), the large unilamellar vesicles (LUV), and the cochleate vesicles. A less desirable form are multivesicular liposomes in which one vesicle contains one or more smaller vesicles.

Typically, sEVs as obtained can be injected at the wound margin to increase the process of the wound healing.

As used herein the terms "administering" or "administration" refer to the act of injecting or otherwise physically delivering a substance as it exists outside the body (e.g., sEVs containing CD98hc) into the subject, such as by mucosal, intradermal, intravenous, subcutaneous, intramuscular delivery and/or any other method of physical delivery described herein or known in the art. When a disease, or a symptom thereof, is being treated, administration of the substance typically occurs after the onset of the disease or symptoms thereof. When a disease or symptoms thereof, are being prevented, administration of the substance typically occurs before the onset of the disease or symptoms thereof. In the context of the invention, the subject is administered of sEVs containing CD98hc according to the invention by topical administration.

A "therapeutically effective amount" is intended for a minimal amount of active agent which is necessary to impart therapeutic benefit to a subject. For example, a "therapeutically effective amount" to a subject is such an amount which induces, ameliorates or otherwise causes an improvement in the pathological symptoms, disease progression or physiological conditions associated with or resistance to succumbing to a disorder. It will be understood that the total daily usage of the compounds of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidential with the specific compound employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The present invention relates also to a pharmaceutical composition comprising the sEVs containing CD98hc as described above. The sEVs containing CD98hc may be combined with pharmaceutically acceptable excipients, and optionally sustained-release matrices, such as biodegradable polymers, to form pharmaceutical compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to one or more of the following agents: solvents such as olive oil, olive oil refined, cottonseed oil, sesame oil, sunflower seed oil, peanut oil, wheat germ oil, soybean oil, jojoba oil, evening primrose oil, coconut oil, palm oil, sweet almond oil, aloe oil, apricot kernel oil, avocado oil, borage oil, hemp seed oil, macadamia nut oil, rose hip oil, pecan oil, hazelnut oil, sasanqua oil, rice bran oil, shea butter, corn oil, camellia oil, grape seed oil, canola oil, castor oil, and combinations thereof, preferably olive oil refined, emulsifiers, suspending agents, decomposers, binding agents, excipients, stabilizing agents, chelating agents, diluents, gelling agents, thickening agent such as beeswax and/or petroleum jelly, preservatives, lubricants, absorption delaying agents, liposomes, antioxidants such as butylhydroxytoluene or butylhydroxyanisole, and the like. The pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Particularly, the pharmaceutical composition is formulated into a topical formulation that can be directly applied to the skin, for example, a skin suffering from skin afflictions. The topical formulation suitable for the pharmaceutical composition may be an emulsion, a gel, an ointment, a cream, a patch, an embrocation, an aerosol, a spray, a lotion, a serum, a paste, a foam, or a drop. In one embodiment of this application, the pharmaceutical composition is formulated into an external preparation by admixing the extract according to this application with a base such as those that are well known and commonly used in the art.

In some embodiment, the small extracellular vesicles (sEV) comprising CD98hc of the present invention is administered to the subject in combination with another active ingredient. In some embodiment, the small extracellular vesicles (sEV) comprising CD98hc of the present invention is administered to the subject in combination with a standard treatment of skin afflictions. For instance, standard treatment of skin afflictions is selected from the group consisting of antihistamines; vitamins such as retinoid and vitamin D; steroids; cyclosporine; adalimumab; brodalumab; etanercept; guselkumab; infliximab; ixekizumab; secukinumab; ustekinumab; apremilast, topical or oral antibiotics such as cephalexin, ciprofloxacin, dicloxacillin, flucloxacillin, erythromycin, amoxicillin and mupirocin; topical immunomodulators such as elidel and protopic; topical coal tar; benzoyl peroxide; glycolic acid; salicylic acid; sulfur; topical corticosteroids such as clobetasol propionate, betamethasone valerate, betamethasone diproprionate, prednisone, prednisolone or hydrocortisone; topical calcineurin inhibitors such as tacrolimus or pimecrolimus; topical JAK inhibitors; topical WNT agonists; topical GSK3b inhibitors; phenylalanine; psolarens such as oxsoralen or trisoralen; topical antifungals such as ketoconazole, nystatin, naftifine, tolnaftate, miconazole, undecyclenic acid, econazole, ciclopirox, oxiconazole, sertaconazole, efinaconazole, tavaborole, terbinafine, clotrimazole, sulconazole, butenafine, luliconazole; phototherapy such as Nb UVB, PUVA, excimer laser or lamp, laser resurfacing and light therapy methotrexate.

The invention will be further illustrated by the following figures and examples. However, these examples and figures should not be interpreted in any way as limiting the scope of the present invention.

FIGURES

Figure 1B:
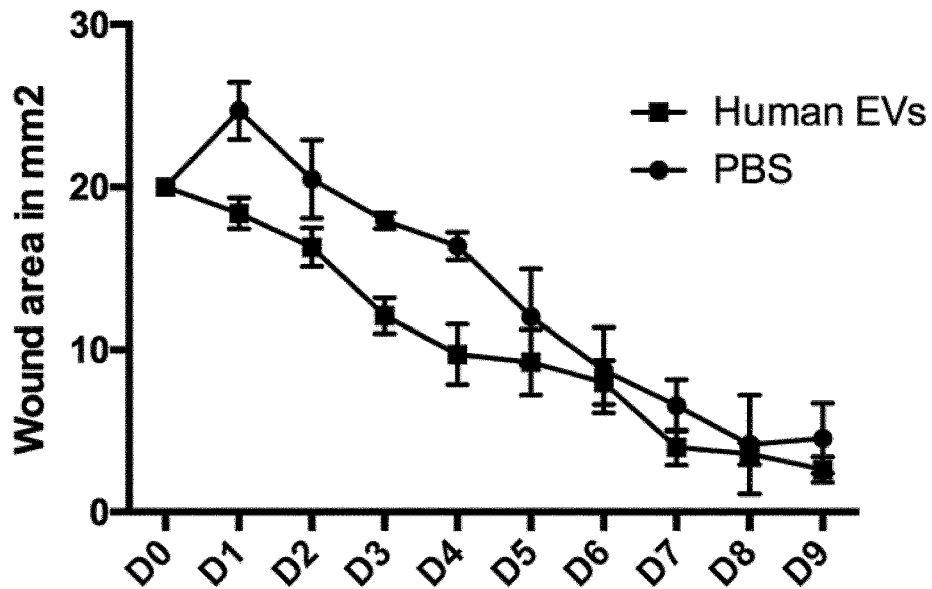

FIG. 1: The transmembrane protein CD98hc transferred by EVs is functional in vivo. A) In vivo rescue of epidermal CD98hc KO mice wound closure defect (4OHT treated-K14CreERT2, CD98hcfl/fl, Boulter al, 2013) was observed when human DF-EVs were subcutaneously injected at day 0 (D0) around the wound margins (4 distinct sites). Wound closure was measured for 7 days. Healing process was enhanced when wound edges were injected with EVs (significant at D2 and D3, black square) compared to PBS injection (black circle). B) Wound closure was also improved in WT elderly mice (24-27 months-old) when injected subcutaneously at day 0 (D0) around the wound margins (4 distinct sites, (significant at D2, D3 and D4). Wound closure is impaired in elderly mice and was thus followed for 9 days. Data represented are means ($\pm$s.e.m; p value *p>0.05, **p<0.01; n≥3 per time point).

Figure 2:
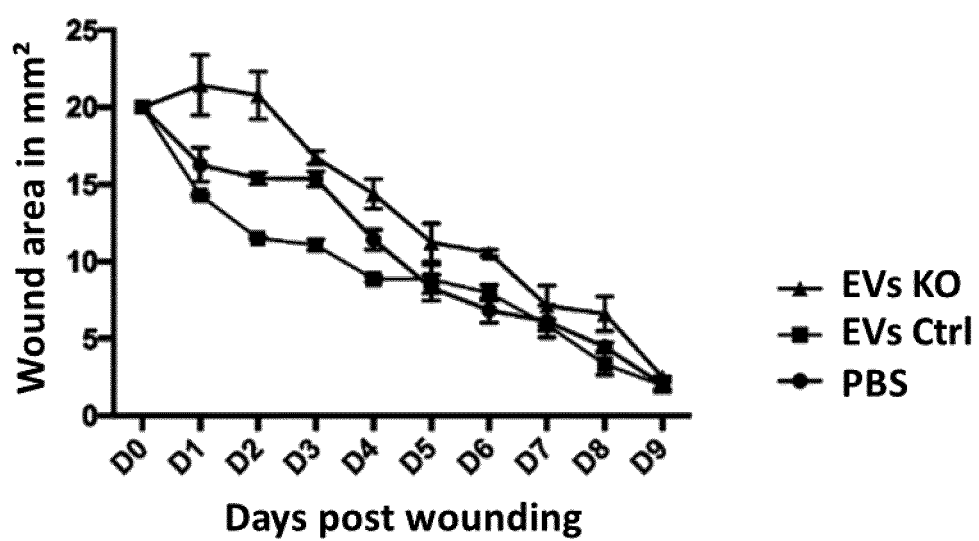

FIG. 2: The transmembrane protein CD98hc transferred by EVs improves wound closure in vivo. Acceleration of epidermal wound closure in wild-type elderly mice (24-26 months-old) following subcutaneous injection at day 0 (D0) of DF-EVs isolated from murine dermal fibroblasts (DF) expressing CD98hc (EVs Ctrl, black rectangle) compared to DF-EVs KO for CD98hc (i.e. EVs isolated from murine dermal fibroblasts deficient for CD98hc) (EVs KO, black triangle). Injections were performed around the wound margins (4 distinct sites). Wound closure was measured for 9 days. Healing process was enhanced when wound edges were injected with EVs expressing CD98hc compared to EVs deprived of CD98hc. PBS injection correspond to control conditions (PBS, black circle). Wound closure is impaired in elderly mice compared to young mice and was thus followed for 9 days. Data represented are means ($\pm$s.e.m; p value *p>0.05, **p<0.01; n≥3 per time point).

EXAMPLE

Material & Methods

Mice

All procedures were approved by the Institutional Animal Care and Use Committee at the University of Nice-Sophia Antipolis (Nice, France; Agreement NCE/66 and NCE/284). K14-CreERT2, CD98hcfl/fl have been described previously (Boulter et al. 2013).

Cell Culture

Dermal mouse fibroblasts were isolated from Fsp1Cre, CD98hcfl/fl (Fsp1Cre from The Jackson Laboratory Stock No: 012641) or CD98hcfl/fl young adult skin (3-month-old) and cultured in the following medium: DMEM high glucose, 20 mM Hepes, 2 mM glutamine, 0.1 mM beta-mercaptoethanol, 10% inactivated SVF, 0.1 mM essential amino acid. After 1 passage, fibroblasts were immortalized with SV40 large T antigen (Keriel et al., 2015). During EVs transfer experiment, cells were cultured in medium with EVs-depleted serum EVs-depleted serum was prepared by overnight 100,000×g ultracentrifugation.

sEVs Isolation sEVs were isolated by differential ultracentrifugation as described in Théry et al., 2001, from murine dermal fibroblasts or human dermal fibroblasts (either expressing CD98hc or KO for CD98hc) following O/N serum starvation. Briefly, 24 h serum free conditioned media was centrifugated at 300×g during 10 min to pellet cells. Supernatant was centrifugated at 2000×g during 20 min, transferred to new tubes and centrifugated in a 45Ti rotor (Beckman) during 40 min at 10,000×g and finally at 100,000×g during 90 min. The pellet was then washed in PBS and centrifugated at 100,000×g during 90 min. The pellet was resuspended in EVs-free PBS. The particle size distribution and concentration of sEvs were identified by NanoSight LM10 HS (Malvern Instruments).

sEVs Treatment In Vitro

Dermal fibroblast cultured in EV-depleted medium were treated with isolated sEVs during 24 hours with approximately the ratio of $24.10^9$ particles for $1.10^5$ recipient cells.

DF Tracks Acquisition and Analysis

DF were treated for 24 hours with EV, then imaged in phase-contrast every 3 minutes for 18 hours on Highthroughput Live Epifluorescence Microscope (ZEISS) using AxioVision® software (ZEISS). Cell tracks were analyzed using Manual Tracking and Chemotaxis Tools Image J's plugins.

Flow Cytometry Analysis

Immunolabeled cells were analyzed on a flow cytometer (FACSCalibur; BD) with CellQuest software (BD). Staining of single DF suspension was performed using either PE-coupled primary antibody against mouse CD98hc (eBioscience, clone RL388) or against human CD98hc using C13 (hybridoma) primary antibody and Alexa Fluor—fluorescein anti-mouse antibody (Invitrogen).

Histology and Immunohistochemistry

Five Tm formalin-fixed paraffin-embedded tissue sections were stained for human-CD98hc (Santa Cruz, clone H-300) and Alexa Fluor-594 conjugated anti-rabbit (Invitrogen). Nucleus were stained with DAPI (Sigma-Aldrich) (Boulter et al., 2013).

In Vivo Wound Healing

Mice were topically treated with 4-hydroxy-tamoxifen at P19 to induced CD98hc deletion in basal keratinocytes as previously described (Boulter et al., 2013). At P65, mice were anesthetized by isoflurane inhalation. Balb/c mice from 24 to 26 months old were used to determine the effect of DF-EV CD98hc$^{+/+}$ vs. DF-EV CD98hc$^{-/-}$. A 5-mm-punch biopsy was performed on the back trimmed skin, followed by four 15 microlitters-injections of either PBS-sEVs ($1.10^{10}$ sEVs per mouse) or PBS only at the wound margins. Pictures were taken daily and used to measure wound area. Tissue samples were collected and processed (paraffin-embedded) at day 9 as previously reported (Boulter et al., 2013). This experiment was also performed on elderly mice (24-27 months old), except pictures were taken every day for 9 days, at which mice were sacrificed.

Statistical Analysis

Cell culture experiments were performed at least three times. For in vivo experiments, Monte-Carlo simulation was used to determine group size. All mouse experiments were performed in a blinded fashion. All quantifications represent mean±standard error of the mean (s.e.m.). Images are representative of experiments that have been repeated at least three times. Group comparison was performed using two-tailed unpaired Student's t test.

Results

We first characterized the small EVs (sEVs) produced by WT (CD98hcfl/fl) or KO for CD98hc (Fsp1Cre, CD98hcfl/fl) dermal fibroblast (DF) (Keriel et al., 2015). To do so, conditioned media were collected from DF after 24 hours of incubation in medium without serum. sEVs were isolated by differential ultracentrifugation, as described in Théry et al., 2001.

The sEVs correspond to the pellet obtained after 100,000×g ultracentrifugation, as defined by Kowal et al., 2016 who performed proteomic comparisons of EVs population. Exosomes are part of this population of sEVs (Kowal et al., 2016). The particle size distribution and concentration were measured by Nano Sight analysis (data not shown). WT and KO DF produced comparable amounts of particles (WT $1,613.10^9$ particles/$10^6$ cells±$3,023.10^8$; KO $1,191.10^9$ particles/$10^6$ cells±$1.57.10^8$) indicating that CD98hc is dispensable for EV biogenesis (data not shown). Profile of size distribution of sEVs isolated from WT and KO dermal fibroblast confirmed that we isolated sEVs (data not shown). Previous studies demonstrated sEV production by cancer associated fibroblasts in numerous cancers (Boelens et al., 2014; Yeung et al., 2016).

Here, we show that sEVs are also produced and secreted by healthy adult DF. To assess if CD98hc is transferred via sEVs, we incubated sEVs, produced from WT DF for 24 hours, with CD98hc KO DF (data not shown). CD98hc expression at the cell surface was then analyzed by flow cytometry (data not shown). Interestingly, we observed a reconstitution of CD98hc expression (66%) in KO DF when incubated with WT sEVs. This effect was increased when KO DF were incubated with sEVs produced by KO DF reconstituted with human CD98hc (sEVs4F2) (99% of CD98hc positives cells). This could be explained by the fact that human CD98hc was overexpressed compared to endogenous murine CD98hc on WT DF cells. Thus, the more CD98hc is expressed at the membrane, the more efficient it is transferred. As expected, KO DF did not express CD98hc even when incubated with sEVs produced by KO DF (data not shown). Altogether, we demonstrate that the transmembrane protein CD98hc is transferred via sEVs, but is not required to generate them. We then assessed if the transferred CD98hc was functional. As a mediator of integrin signaling, CD98hc is involved in cell migration (Feral et al., 2005). Consistent with this finding, KO DF displayed a strong migration defect compared to WT cells (cell track measurement for 18 hours, data not shown). Strikingly, this defect was rescued by the incubation of KO DF with sEVs isolated from WT DF, or sEVs isolated from human CD98hc reconstituted DF. Hence, CD98hc is functionally transferred by sEVs in vitro.

We establish here that the regulator of integrin signaling pathways, CD98hc, is transferred in sEVs in non-pathological conditions and participates to cell-cell communication. CD98hc and its associated integrins might be transferred as a hub of signalization via sEVs which could act as a highly efficient signaling platform. Next, to determine whether the CD98hc transfer via sEVs was also functional in vivo, sEVs produced by human DF were injected at the wound margins of K14CreERT2, CD98hcfl/fl mice. The injection of sEVs significantly rescued the wound closure defect compared to the mice injected with PBS only (FIG. 1). Immunofluorescence staining of human CD98hc performed 7 days post-wounding confirmed the transfer of hCD98hc from injected sEV to local keratinocytes and DF. Moreover, CD98hc expression was stabilized at least 7 days after injection allowing CD98hc expression reconstitution in vivo. Next, we tested whether elderly mice, described to present defect in wound closure, and which skin showed decrease expression of CD98hc in both basal keratinocytes and dermal fibroblasts, could benefit from such EVs injection. We found that EVs injection post wounding favored wound closure specifically in the early step (up to day 5) compared to PBS injection. Healing process was enhanced when wound edges were injected with EVs expressing CD98hc compared to EVs deprived of CD98hc (FIG. 2). Thus, CD98hc was not only functionally transferred via extracellular vesicles both in vitro and in vivo (in both CD98hc KO mice and WT aging conditions) but was required to improve wound closure in elderly mice in vivo (WT aging conditions injected with EV expressing CD98hc vs. EV deficient for CD98hc). sEVs derived from induced pluripotent stem cell-derived mesenchymal stem cells (Zhang et al., 2015) or from adipose mesenchymal stem cells (Hu et al., 2016) were shown to improve wound healing by optimizing the characteristics of fibroblasts. However, the mediator transported by sEVs responsible for the improvement of the wound closure remains unidentified. Here, we demonstrate that CD98hc transfer via sEVs improved wound healing by targeting both keratinocytes and fibroblasts in vivo. These results are in good agreement with recent work showing EVs derived from mesenchymal stem cell promotes in vivo hair follicle growth in mice (Rajendran et al., 2017). Our data highlights CD98hc potential role in the reciprocal crosstalk between keratinocytes and fibroblasts during wound healing. Moreover, CD98hc is overexpressed in many cancers, including epithelial cancer (Estrach et al., 2014; Nguyen et al., 2011; Prager et al., 2009). CD98hc containing EV transfer could be crucial in epithelial/mesenchyme interaction in tumor initiation (Arwert et al., 2012), opening novel question on the involvement sEVs in epithelial cancer progression.

Altogether, we show that, while its expression is dispensable to generate EV, CD98hc is functionally transferred to recipient cells both in vitro and in vivo. sEV injection in vivo allowed functional CD98hc transfer leading to improved wound closure. Overall, our study provides novel insights in EV based intercellular communication in skin via the transmembrane protein CD98hc, which could lead to potential therapeutic advance skin afflictions.

REFERENCES

Throughout this application, various references describe the state of the art to which this invention pertains. The disclosures of these references are hereby incorporated by reference into the present disclosure.

Arwert, E. N., Hoste, E., and Watt, F. M. (2012). Epithelial stem cells, wound healing and cancer. Nat. Rev. Cancer 12, 170-180.

Boelens, M. C., Wu, T. J., Nabet, B. Y., Xu, B., Qiu, Y., Yoon, T., Azzam, D. J., Twyman-Saint Victor, C., Wiemann, B. Z., Ishwaran, H., et al. (2014). Exosome transfer from stromal to breast cancer cells regulates therapy resistance pathways. Cell 159, 499-513.

Boulter, E., Estrach, S., Errante, A., Pons, C., Cailleteau, L., Tissot, F., Meneguzzi, G., and Féral, C. C. (2013). CD98hc (SLC3A2) regulation of skin homeostasis wanes with age. J. Exp. Med. 210, 173-190.

Colombo, M., Raposo, G., and Théry, C. (2014). Biogenesis, Secretion, and Intercellular Interactions of Exosomes and Other Extracellular Vesicles. Annu. Rev. Cell Dev. Biol. 30, 255-289.

Estrach, S., Lee, S.-A., Boulter, E., Pisano, S., Errante, A., Tissot, F. S., Cailleteau, L., Pons, C., Ginsberg, M. H., and Féral, C. C. (2014). CD98hc (SLC3A2) Loss Protects Against Ras-Driven Tumorigenesis by Modulating Integrin-Mediated Mechanotransduction. Cancer Res. 74, 6878-6889.

Feral, C. C., Nishiya, N., Fenczik, C. A., Stuhlmann, H., Slepak, M., and Ginsberg, M. H. (2005). CD98hc (SLC3A2) mediates integrin signaling. Proc. Natl. Acad. Sci. U.S.A. 102, 355-360.

Hu, L., Wang, J., Zhou, X., Xiong, Z., Zhao, J., Yu, R., Huang, F., Zhang, H., and Chen, L. (2016). Exosomes derived from human adipose mensenchymal stem cells accelerates cutaneous wound healing via optimizing the characteristics of fibroblasts. Sci. Rep. 6, srep32993.

Keriel, A., Botella, E., Estrach, S., Bragagnolo, G., Vergunst, A. C., Feral, C. C., and O'Callaghan, D. (2015). Brucella Intracellular Life Relies on the Transmembrane Protein CD98 Heavy Chain. J. Infect. Dis. 211, 1769-1778.

Kowal, J., Arras, G., Colombo, M., Jouve, M., Morath, J. P., Primdal-Bengtson, B., Dingli, F., Loew, D., Tkach, M., and Théry, C. (2016). Proteomic comparison defines novel markers to characterize heterogeneous populations of extracellular vesicle subtypes. Proc. Natl. Acad. Sci. 113, E968-E977.

Nguyen, H. T. T., Dalmasso, G., Torkvist, L., Halfvarson, J., Yan, Y., Laroui, H., Shmerling, D., Tallone, T., D'Amato, M., Sitaraman, S. V., et al. (2011). CD98 expression modulates intestinal homeostasis, inflammation, and colitis-associated cancer in mice. J. Clin. Invest. 121, 1733-1747.

Prager, G. W., Poettler, M., Schmidinger, M., Mazal, P. R., Susani, M., Zielinski, C. C., and Haitel, A. (2009). CD98hc (SLC3A2), a novel marker in renal cell cancer. Eur. J. Clin. Invest. 39, 304-310.

Rajendran, R. L., Gangadaran, P., Bak, S. S., Oh, J. M., Kalimuthu, S., Lee, H. W., Baek, S. H., Zhu, L., Sung, Y. K., Jeong, S. Y., et al. (2017). Extracellular vesicles derived from MSCs activates dermal papilla cell in vitro and promotes hair follicle conversion from telogen to anagen in mice. Sci. Rep. 7, 15560.

Singh, A., Fedele, C., Lu, H., Nevalainen, M. T., Keen, J. H., and Languino, L. R. (2016). Exosome-mediated Transfer of αvβ3 Integrin from Tumorigenic to Nontumorigenic cells Promotes a Migratory Phenotype. Mol. Cancer Res. MCR 14, 1136-1146.

Théry, C., Amigorena, S., Raposo, G., and Clayton, A. (2001). Isolation and Characterization of Exosomes from Cell Culture Supernatants and Biological Fluids. In Current Protocols in Cell Biology, (John Wiley & Sons, Inc.).

Yeung, C. L. A., Co, N.-N., Tsuruga, T., Yeung, T.-L., Kwan, S.-Y., Leung, C. S., Li, Y., Lu, E. S., Kwan, K., Wong, K.-K., et al. (2016). Exosomal transfer of stroma-derived miR21 confers paclitaxel resistance in ovarian cancer cells through targeting APAF1. Nat. Commun. 7, ncomms11150.

Zhang, J., Guan, J., Niu, X., Hu, G., Guo, S., Li, Q., Xie, Z., Zhang, C., and Wang, Y. (2015). Exosomes released from human induced pluripotent stem cells-derived MSCs facilitate cutaneous wound healing by promoting collagen synthesis and angiogenesis. J. Transl. Med. 13.

The invention claimed is:

1. A method for treating a skin affliction in a subject comprising a step of administering to said subject a therapeutically effective amount of small extracellular vesicles (sEV) comprising CD98hc.

2. The method according to claim 1, wherein, the sEV are exosomes.

3. The method according to claim 1, wherein, the sEV are nanoparticles.

4. The method according to claim 1, wherein, the sEV are liposomes.

5. The method according to claim 1, wherein, the administration of sEV is performed by topical administration.

6. The method according to claim 1, wherein the skin affliction is a wound.

7. The method according to claim 6 wherein the method improves healing of the wound.

8. The method according to claim 6, wherein subject is an elderly person.

9. The method according to claim 1, wherein the step of administering is performed in combination with a standard treatment of skin afflictions.

* * * * *